United States Patent [19]
Chetverin et al.

[11] Patent Number: 5,958,698
[45] Date of Patent: Sep. 28, 1999

[54] METHOD FOR AMPLIFICATION AND EXPRESSION OF NUCLEIC ACIDS IN SOLID MEDIA AND ITS APPLICATION FOR NUCLEIC ACID CLONING AND DIAGNOSTICS

[75] Inventors: Alexander Borisovich Chetverin; Helena Vladimirovna Chetverina, both of Moskovskaya oblast, Russian Federation

[73] Assignee: Institut Belka, Russian Federation

[21] Appl. No.: 09/135,446

[22] Filed: Aug. 17, 1998

Related U.S. Application Data

[60] Continuation of application No. 08/723,260, Sep. 30, 1996, which is a division of application No. 07/966,713, Oct. 26, 1992, Pat. No. 5,616,478.

[51] Int. Cl.$^6$ .............................. C12Q 1/68; C12P 19/34
[52] U.S. Cl. ................................. 435/6; 435/91.2
[58] Field of Search ............................ 435/6, 91.1, 91.2, 435/299

[56] References Cited

U.S. PATENT DOCUMENTS

| | | | |
|---|---|---|---|
| 4,965,188 | 10/1990 | Mullis et al. | 435/91 |
| 5,004,543 | 4/1991 | Pluskal et al. | 210/490 |
| 5,188,963 | 2/1993 | Stapleton | 435/299 |
| 5,190,864 | 3/1993 | Giese et al. | 435/41 |
| 5,382,511 | 1/1995 | Stapleton et al. | 435/6 |

FOREIGN PATENT DOCUMENTS

1472505 A1  4/1989  Russian Federation .

OTHER PUBLICATIONS

Bucke, C., "Cell Immobilization In Calcium Alginate," Methods In Enzymology 135: 175–189 (1987).
Chetverina, H.V. and Chetverin, A.B., "Cloning of RNA Molecules In Vitro," Nucleic Acids Research 21, No. 10: 2349–2353 (1993).
Klibanov, A.M., "Immobilized Enzymes And Cells As Practical Catalysts," Science 219: 722–727 (1983).
Nilsson, K. et al., "Entrapment of Microbial And Plant Cells In Beaded Polymers," Methods In Enzymology 135: 222–230 (1987).
O'Driscoll, K.F., "Techniques of Enzyme Entrapment In Gels," Methods In Enzymology 44: 169–183 (1976).
Walker, G.T. et al., "Strand Displacement Amplification—an Isothermal, In Vitro DNA Amplification Technique," Nucleic Acids Research 20: 1691–1696 (1992).
Chang, T.M.S., "Microencapsulation of Enzymes And Biologicals," Methods In Enzymology 44: 201–218 (1976).
Chibata, I., "Immobilization of Cells In Carrageenan," Methods In Enzymology 135: 189–198 (1987).
Kramer, F.R. and Lizardi, P.M., "Replicatable RNA Reporters," Nature 339: 401–402 (1989).
Nojima, S. and Yamada, T., "Large–Scale Production of Photo–Cross–Linkable Resin Immobilized Yeast And Its Application To Industrial Ethanol Production," Methods In Enzymology 136: 380–394 (1987).

Primrose, S.B., "Cell and Enzyme Immobilization," Modern Biotechnology, Chapter 7, Blackwell Scientific Publications (Oxford, 1987).
Saiki, R.K. et al., "Primer–Directed Enzymatic Amplification of DNA With A Thermostable DNA Polymerase," Science 239: 487–491 (1988).
Maniatis et al., "Molecular Cloning,": 161 (1982).
Guatelli et al., "Isothermal, In Vitro Amplification of Nucleic Acids," Proc. Natl. Acad. Sci. U.S.A. 87: 1874–1878 (1990).
Erlich, H.A. et al., "Recent Advances . . . ," Science 252: 1643–1651 (1991).
Haruna, I. et al., "Autocatalytic Synthesis . . . ," Science 150: 884–886 (1965).
Kamen, R.I., "Structure And Function . . . ," In RNA Phages: 203–234 (1975).
Levisohn, R. et al., "The Cloning of A . . . ," Proc. National Academy Science, U.S.A. 60: 866–872 (1968).
Lizardi, P.M. et al., "Exponential Amplification . . . ," Bio/Technology 6: 1197–1202.
Lomell, H. et al., "Quantitative Assays . . . ," Clin. Chem. 35: 1826–1831 (1989).
Miele, A.A. et al., "Autocatalytic Replication . . . ," J. Mol. Biology 171: 281–295 (1983).
Mullis, K.B. et al., "Specific Synthesis of DNA . . . ," Methods Enzymology 155: 335–350 (1987).
Munishkin, A.V. et al., "Efficient Templates . . . ," Biochemistry 30: 7661–7666 (1991).
Saiki, R.K. et al., "Enzymatic Amplification . . . ," Science 230: 1350–1354 (1985).
Sumper, M. et al., "Evidence for De Novo . . . ," Proc. National Academy Science U.S.A.: 162–166 (1975).
Wu, Y. et al., "Amplifiable Messenger RNA," Proc. National Academy Science U.S.A. (1992).
Anderson, C.W. et al., "Preparation of A Cell–Free . . . ," Methods Enzymology 101: 635–644 (1983).
Baranov, V.I. et al., "Gene Expression . . . ," Gene 84: 463–466 (1989).
Bujard, H. et al., "A T5 Promoter–Based . . . ," Methods Enzymology 155: 416–433 (1987).
Chambliss, G.H. et al., "Bacterial In Vitro . . . ," Methods Enzymology 101: 598–605 (1983).

(List continued on next page.)

*Primary Examiner*—Eggerton A. Campbell
*Attorney, Agent, or Firm*—Fish & Richardson P.C.

[57] ABSTRACT

Amplification and/or expression of nucleic acids is carried out in a medium immobilized by using an organic and/or inorganic solid matrix penetrating the medium and having a porous, fibrous, reticulated, coiled, capillary, lamellar or folded texture and which includes the components of a cell-free enzyme system of exponential amplification of nucleic acids and/or components of a cell-free enzyme system of nucleic acid expression. In this medium, the progeny of each molecule (clone) and the expression products remain in the same zone of the reaction volume where the matrix molecule was initially located. The method permits cloning of nucleic acids in vitro as well as detection of solitary nuleic acid molecules in the sample studied.

25 Claims, 4 Drawing Sheets

OTHER PUBLICATIONS

Chen, H.–Z. et al., "Prokaryotic Coupled . . . ," Methods Enzymology 101: 674–690 (1983).

Lesley, S.A. et al., "Use of In Vitro . . . ," J. Biol. Chem. 266: 2632–2638 (1991).

Merrick, W.C. "Translation of Exogenous . . . ," Methods Enzymology 101: 606–615 (1983).

Tymms, M.J., et al., "Efficient In Vitro . . . ," Gene, Anal. Tech. 5: 9–15 (1988).

Chetverin, Alexander B. et al., "On The Nature of Spontaneous RNA Synthesis by QB Replicase," J. Mol. Biol. 222: 3–9 (1991).

Myers, T.W., et al., "Reverse Transcription . . . ," Biochemistry 30: 7661–7666 (1991).

Munishkin, A.V. et al., "Efficient Templates . . . ," J. Mol. Biol. (1991) 221, pp. 463–472.

METHOD FOR AMPLIFICATION AND EXPRESSION OF NUCLEIC ACIDS IN SOLID MEDIA AND ITS APPLICATION FOR NUCLEIC ACID CLONING AND DIAGNOSTICS

This is a continuation of copending application Ser. No. 08/723,260, filed Sep. 30, 1996, allowed but not issued, which is a division of application Ser. No. 07/966,713, filed Oct. 26, 1992, now U.S. Pat. No. 5,616,478.

FIELD OF THE INVENTION

This invention is in the field of amplification, expression, cloning, and diagnostics of nucleic acids.

BACKGROUND OF THE INVENTION

Several methods for exponential amplification of nucleic acids in vitro have been invented so far. These are: RNA amplification by viral RNA-directed RNA polymerases (VRP), DNA amplification in polymerase chain reaction (PCR), and isothermal multienzyme (3SR) amplification of nucleic acids. In contradistinction to linear amplification, such as which takes place during RNA synthesis with a DNA-directed RNA polymerase, the number of nucleic acid molecules increases in an exponential amplification reaction as an exponential function of the elapsed time, thus allowing a large amount of nucleic acid to be obtained in a short time period starting with a low number of nucleic acid templates. Currently, an exponential amplification reaction is carried out in a liquid reaction medium that contains the components of a cell-free enzyme system comprising a reaction buffer, appropriate enzyme(s), nucleotide substrates, and, when required, polymerization primers. In this format, the product nucleic acids synthesized on each template are allowed to spread all over the reaction medium.

In VRP reaction, exponential synthesis occurs because the product and template RNAs remain single-stranded during RNA synthesis, and both serve as equally effective templates in the next round of synthesis. Thus, the number of templates doubles after each round of replication unless RNA is in molar excess over the replicase [Haruna, I. and Spiegelman, S. (1965). Autocatalytic Synthesis of a Viral RNA in vitro. Science 150, 884–886; Kamen, R. I. (1975). Structure and Function of the Qβ RNA Replicase. In RNA Phages (Zinder, N. D., ed.), pp. 203–234, Cold Spring Harbor Laboratory Press, Cold Spring Harbor, N.Y.]. Viral RNA-directed RNA polymerases, such as Qβ replicase, demonstrate a strict template specificity which is achieved through recognition by the enzyme of special structures that are present in their specific templates and are absent in other RNAs. RNAs containing these structures are called "replicating RNAs". Munishkin, A. V., Voronin, L. A., Ugarov, V. I., Bondareva, L. A., Chetverina, H. V. and Chetverin, A. B. (1991). Efficient Templates for Qβ replicase are Formed by Recombination from Heterologous Sequences. J. Mol. Biol. 221, 463–472. Foreign nucleic acid can be made amplifiable with a VRP by providing the nucleic acid in the form of replicating RNA, for example, by inserting the corresponding nucleotide sequence into a naturally occurring replicating RNA [Miele, A. A., Mills, D. R. and Kramer, F. R. (1983). Autocatalytic Replication of a Recombinant RNA. J. Mol. Biol. 171, 281–295; Wu, Y., Zhang, D. and Kramer, F. R. (1992). Amplifiable Messenger RNA. Proc. Natl. Acad. Sci. U.S.A., in press]. VRP reaction is carried out at a constant temperature and is very fast: in a 30-min incubation, the number of RNA templates in the Qβ replicase reaction increases $10^9$-fold [Lizardi, P. M. Guerra, C. E., Lomeli, H., Tussie-Luna, I. and Kramer, F. R. (1988). Exponential Amplification of Recombinant-RNA Hybridization Probes. Bio/Technology 6, 1197–1202].

PCR is used for the in vitro amplification of DNA. This reaction requires the annealing and enzymatic extension of two oligonucleotide primers that embrace a region within a DNA molecule to be amplified (a target region), and that use complementary strands of the DNA as templates for extension by a DNA polymerase, their growing 3' termini being directed towards each other. The word "embrace" is used here to describe the property of the primers to anneal on complementary strands of the DNA downstream from the target region. Unlike VRP reaction, the product strand in PCR is involved in a duplex with the template. Therefore, the template and product strands have to be melted apart at elevated temperature to initiate the next round of replication where each strand anneals with one of the primers and serves as a template for additional replication. The process is repeated many times by cycling between the annealing and melting temperatures, resulting in an exponential amplification of the target region [Saiki, R. K., Scharf, S., Faloona, F., Mullis, K. B., Horn, G. T., Erlich, H. A. and Arnheim, N. (1985). Enzymatic Amplification of β-Globin Genomic Sequence and Restriction Site Analysis for Diagnosis of Sickle Cell Anemia. Science 230, 1350–1354; Mullis, K. B. and Faloona, F. A. (1987). Specific Synthesis of DNA in vitro via a Polymerase-catalyzed Chain Reaction. Methods Enzymol. 155, 335–350]. Currently, PCR is carried out with the use of a thermostable DNA polymerase that remains active after the reaction mixture is heated to 95–100° C. to melt DNA strands apart [Erlich, H. A., Gelfard, D. and Sninsky, J. J. (1991). Recent Advances in the Polymerase Chain Reaction. Science 252, 1643–1651]. Because of the need for temperature cycling, PCR requires special equipment and is about an order of magnitude slower than VRP reaction. At the same time, PCR allows any desirable DNA to be amplified by virtue of having two specific primers, and without the need for preparing a recombinant molecule.

Recently, isothermal amplification of nucleic acids in the multienzyme system (3SR) has been invented that combines the advantages of both the VRP reaction and PCR. 3SR is based on the concerted action of three enzymes: a DNA-directed RNA polymerase, a reverse transcriptase, and RNase H, and mimics the replication system of retroviruses. A double-stranded DNA fragment containing an RNA polymerase promoter sequence at each end or a single-stranded RNA can serve as a primary template. A DNA-directed RNA polymerase, such as T7 RNA polymerase, uses double-stranded DNA molecule to linearly synthesize multiple single-stranded RNA copies of the DNA target region included between the RNA polymerase promoters. A reverse transcriptase, such as that of the avian myeloblastosis virus (AMV), makes double-stranded cDNA copies of the RNA transcripts using primers that are complementary to the 3' termini of the transcripts, and that include the RNA polymerase promoter sequence to restore the sequence at each end of the cDNAs. RNase H destroys the RNA template involved in the RNA:DNA heteroduplex after the first-strand cDNA synthesis, enabling the second strand of the cDNA to be synthesized. The action of RNA polymerase and RNase H results in the formation of single-stranded templates, allowing the amplification to proceed exponentially without temperature cycling. 3SR reaction is as fast as VRP reaction, and like PCR it is not restricted to specific templates. The product of 3SR reaction is a mixture of double-stranded DNA and single-stranded RNA molecules. Guatelli, J. C., Whitfield, K. M., Kwoh, D. Y., Barringer, K. J., Richman, D. D. and Gingeras, T. R. (1990). Isothermal, in vitro Amplification of Nucleic Acids by a Multienzyme Reaction Modeled after Retroviral Replication. Proc. Natl. Acad. Sci. U.S.A. 87, 1874–1878.

Due to the exponential nature of the amplification reactions discussed above, each of them can theoretically be employed to obtain in a short time a great number of progeny molecules starting with a single nucleic acid template. If realized, this would allow nucleic acids to be cloned in vitro, providing a powerful alternative to the conventional DNA cloning in microbial cells. Also, this would provide for an absolute method for nucleic acid diagnostics. For example, even if a single molecule of a viral, microbial, or oncogenic nucleic acid occurred in an analyzed sample, it itself, or an amplifiable reporter targeted against it [Kramer, F. R. and Lizardi, P. M. (1989). Replicatable RNA Reporters. Nature 339, 401–402], could be amplified to the amount that is easily detected by conventional techniques. However, neither of these possibilities has been so far realized because of severe practical problems.

Levisohn and Spiegelman claimed that they succeeded in the cloning of RNA molecules using Qβ replicase amplification system. They diluted the RNA template so that less than one molecule was expected per sample, and observed RNA synthesis in roughly half of the samples [Levisohn, R. and Spiegelman, S. (1968). The Cloning of a Self-replicating RNA Molecule. Proc. Natl. Acad. Sci. U.S.A. 60, 866–872]. However, a proper identification of the products was not performed, and the results were later diminished by the finding that RNA synthesis could be observed in Qβ replicase reaction even if no template were added [Sumper, M. and Luce, R. (1975). Evidence for de novo Production of Self-replicating and Environmentally Adapted RNA Structures by Bacteriophage Qβ Replicase. Proc. Natl. Acad. Sci. U.S.A. 72, 162–166]. Recently this spontaneous RNA synthesis was shown to be caused by replicating RNAs that contaminate the environment [Chetverin, A. B., Chetverina, H. V. and Munishkin, A. V. (1991). On the Nature of Spontaneous RNA Synthesis by Qβ Replicase. J. Mol. Biol. 222, 3–9). The background from contaminating RNAs prevented the VRP-based diagnostics from being able to detect solitary nucleic acid molecules, since as many as 100 irrelevant replicating RNAs usually occurred in an average sample [Lizardi et al. (1988), Chetverin et al. (1991), supra]. The practical detection limit in VRP assays is currently $10^3$ to $10^4$ target molecules [Lomeli, H., Tyagi, S., Pritchard, C. G., Lizardi, P. M. and Kramer, F. R. (1989). Quantitative Assays Based on the Use of Replicatable Hybridization Probes. Clin. Chem. 35, 1826–1831].

Contamination problems are also encountered in PCR and 3SR reactions, although they are not so severe as for VRP reactions, since nucleic acid amplification is controlled by the specificity of the two oligonucleotide primers targeted to the template. Most significant in this case is the limited primer specificity: because of mismatches and primer heterogeneity, a non-specific priming occurs to some extent on irrelevant templates contained in the sample, and becomes competing with the specific priming as the number of specific templates goes below a certain level. At least 100 copies of a specific template are currently needed to reliably initiate PCR [Myers, T. W. and Gelfand, D. H. (1991). Reverse Transcription and DNA Amplification by a *Thermus thermophilus* DNA Polymerase. Biochemistry 30, 7661–7666]. It follows that neither the true cloning (i.e., obtaining the progeny of a single molecule), nor the detection of solitary molecules are currently achievable with these techniques.

There are known methods for expressing nucleic acids in vitro. During expression, the genetic information contained in a nucleotide sequence is translated into the aminoacid sequence of a polypeptide. The translation process occurs on ribosomes that use RNA as an informational messenger which is called mRNA. Translation of an mRNA can be carried out in a cell-free enzyme system comprising a reaction buffer, ribosomes, tRNAs, aminoacids, ATP, GTP, and auxiliary proteins, such as aminoacyl-tRNA synthetases and translation factors [Anderson, C. W., Straus, J. W. and Dudock, B. S. (1983). Preparation of a Cell-free Protein-synthesizing System from Wheat Germ. Methods Enzymol. 101, 635–644; Chambliss, G. H., Henkin, T. M. and Leventhal, J. M. (1983). Bacterial in vitro Protein-synthesis Systems. Methods Enzymol. 101, 598–605; Merrick, W. C. (1983). Translation of Exogenous mRNAs in Reticulocyte Lysates. Methods Enzymol. 101, 606–615]. If DNA rather than RNA is provided, it must be transcribed into RNA. In this case, the expression comprises two steps, DNA transcription and RNA translation, and can be carried out in a coupled transcription/translation cell-free enzyme system that comprises, in addition to the components of the translation system, an appropriate DNA-dependent RNA polymerase and the missing ribonucleoside triphosphates [Chen, H.-Z. and Zubay, G. (1983). Prokaryotic Coupled Transcription-translation. Methods Enzymol. 101, 674–690; Bujard, H., Gentz, R., Lanzer, M., Stueber, D., Mueller, M., Ibrahimi, I., Haeuptle, M.-T. and Dobberstein, B. (1987). A T5 Promoter-based Transcription-translation System for the Analysis of Proteins in vitro and in vivo. Methods Enzymol. 155, 416–433; Tymms, M. J. and McInnes, B. (1988). Efficient in vitro Expression of Interferon Analogs Using SP6 Polymerase and Rabbit Reticulocyte Lysate. Gene Anal. Tech. 5, 9–15; Baranov, V. I., Morozov, I. Yu., Ortlepp, S. A. and Spirin, A. S. (1989). Gene Expression in a Cell-free System on the Preparative Scale, Gene 84, 463–466; Lesley, S. A., Brow, M. A. and Burgess, R. R. (1991). Use of in vitro Protein Synthesis from Polymerase Chain Reaction-generated Templates to Study Interaction of *Escherichia coli* Transcription Factors with Core RNA Polymerase and for Epitope Mapping of Monoclonal Antibodies. J. Biol. Chem. 266, 2632–2638]. The known methods for expression of nucleic acids in vitro employ liquid reaction media, so that the expression products (proteins, polypeptides) can freely migrate throughout the media.

SUMMARY OF THE INVENTION

The present invention is based on our discovery that nucleic acid molecules can be, like microorganisms, grown as colonies in an immobilized medium.

According to our invention, the immobilized medium for amplification of nucleic acids comprises a liquid phase entrapped within a solid matrix that possesses a highly expanded surface with the average pore size ranging from 100 $\mu$m to 5 nm, and therefore is capable of preventing convection and intermixing of different zones of the liquid phase. The immobilized medium contains an amplification system comprising a cell-free enzyme system capable of exponentially amplifying the nucleic acids. The enzyme(s) included in the amplification system can be either present in the liquid phase or immobilized on the solid matrix.

Our invention includes a method for amplification of nucleic acids in an immobilized medium. According to the invention, a nucleic acid or a mixture of nucleic acids to be amplified is introduced into the medium during, or subsequent to, its immobilization. The nucleic acid molecules become entrapped somewhere in the medium, and their exponential amplification results in a "colony" within a limited zone surrounding the progenitor template. Each nucleic acid colony comprises individual clone, i.e. the progeny of a single molecule. The method can employ any system of exponential amplification of nucleic acids in vitro, such as VRP reaction, PCR, or 3SR reaction. Provided that the nucleic acid sample has been properly diluted, different colonies occupy separate zones within the immobilized medium, and this allows the respective clones to be observed and handled separately. The method allows nucleic acids to be cloned in vitro, and even solitary molecules of specific nucleic acids to be detected in an analyzed sample, despite contamination of the sample or the medium with irrelevant templates or the occurrence of non-specific priming.

According to the preferred embodiment, amplification of nucleic acids is carried out in at least one thin layer of an immobilized medium, so that the growing colonies are arranged in a two-dimensional pattern. Employing thin layers makes it easier to separately observe and handle individual colonies, and allows replicas of the colony pattern to be prepared, for example, by colony transfer onto a blotting membrane. The replicas can be used for screening the colonies or for any other purpose, or can be stored for further use. If an immobilized medium comprises more than one layer (a sandwich medium), the enzymes and substrates included in the amplification system can be introduced into separate layers, so that the amplification reaction can be initiated at a pre-selected time by contacting the layers. By using a sandwich medium it is also possible to prepare one or more replicas while amplifying nucleic acids and to supplement the medium with new components at a pre-determined reaction time.

According to the preferred embodiment of our method, the solid matrix that immobilizes the medium should be capable of reversible interaction with nucleic acids. The use of matrices modified with positively charged and/or moderately hydrophobic groups is therefore preferred. Such matrices retard the spreading of the colonies caused by diffusion and thus increase the resolving power of the method, especially when amplifying small nucleic acids.

Entrapment of nucleic acids in an immobilized medium according to the invention substantially prevents a competition between different templates, since their progeny is not allowed to spread all over the reaction volume. In particular, this allows individual nucleic acids to be amplified in bulk with the interference from background growth being largely suppressed.

Our invention includes applications of the method for amplification of nucleic acids in immobilized media for extremely sensitive diagnostics of nucleic acids, such as nucleic acids related to viruses, microorganisms, and oncogenes. Nucleic acids in a sample, their segments, or amplifiable reporters generated in the sample in a target-dependent reaction, are amplified in a thin layer of an immobilized medium. The colonies comprised of the nucleic acids containing a particular sequence are then identified, e.g. by hybridizing them with a specific labeled probe. Solitary target molecules can be reliably detected by employing this method, even if the background from unrelated nucleic acids is several orders of magnitude greater.

Our invention includes applications of the method for amplification of nucleic acids in immobilized media for cloning nucleic acids in vitro. According to the invention, nucleic acids are amplified in a thin layer of an immobilized medium to produce colonies. The colonies are screened, for example, by transferring them onto a blotting membrane and hybridizing the membrane with a labeled probe. Alternatively, the colonies are screened by virtue of expressing nucleic acids in a protein synthesis system in vitro.

Our invention also includes methods for expression of nucleic acids in an immobilized medium. The immobilized medium for expressing nucleic acids according to the invention is similar to the immobilized medium used for nucleic acid amplification, with the exception that it contains an expression system comprising a cell-free enzyme system capable of expressing the nucleic acids. The nucleic acids amplified according to this invention or those obtained by any other method can be expressed in the immobilized medium. According to our invention, nucleic acids can also be both amplified and expressed in the same immobilized medium. In this case, the medium contains both the components of an amplification system and of an appropriate expression system. According to the preferred embodiment, nucleic acids are expressed (or both amplified and expressed) in at least one thin layer of an immobilized medium that contains all the components of the protein synthesis system. Expressing nucleic acids in an immobilized medium results in the expression products being accumulated within the zones where the nucleic acid templates are entrapped. Employing immobilized media allows nucleic acid colonies to be easily screened for their expression products either in situ or upon their transfer onto an expression medium with a replica, or a number of nucleic acid samples to be tested in parallel in a single expression reaction. The synthesized polypeptides can be identified in situ or on a replica by an immunoassay, or by their ability to perform specific enzymatic reactions or to bind a specific ligand.

DETAILED DESCRIPTION OF THE INVENTION

The techniques and materials described herein with respect to one embodiment may not be explicitly described in other embodiments. Their application to the several embodiments described herein, however, is understood. All periodicals, patents and other references cited herein are hereby incorporated by reference.

According to our invention, exponential amplification of nucleic acids and/or their expression (hereinafter referred to as a "reaction") is carried out in an immobilized medium, rather than in solution as it is done in the prior art, in order to keep the templates and the reaction products within limited zones at fixed locations of the reaction volume.

An immobilized medium suitable for the reaction according to the invention comprises a liquid water-based phase entrapped within a solid matrix. The solid matrix has a highly expanded surface that penetrates the liquid phase, so that the liquid phase gets substantially motionless (lack of convection and intermixing of different zones of the liquid phase), apparently due to the intermolecular friction and water structuring near the surface. The solid matrix can possess a various texture, such as porous, fibrous, reticulated, coiled, capillary, lamellar, or folded, with the average distance between the nearest surfaces (the "pore" size) ranging from about 100 µm to 5 nm. The upper limit of the pore size should be less then the distance at which the synthesized nucleic acids or proteins can migrate by diffusion during the reaction. (For example, nucleic acids that are about 100 nucleotides in length diffuse at the rate of approximately 1 mm per hour at room temperature, judging from the size of the colonies seen in FIGS. 2A to 2C.) The lower limit should slightly exceed the size of the nucleic acid and/or protein molecules involved in the reaction to ensure their motion required for the reaction. The matrix can be comprised of a three-dimensional network formed by polymeric molecules or their aggregates; pelleted, cemented, sintered, or compressed water-insoluble powder, grains or microcrystals; spongy substances; tightly packed fibers, microcapillaries or folded pellicle, such as a thin polymeric film or metal foil. The materials used for preparing the solid matrix should be chemically inert under the reaction conditions, and the surface should not cause denaturing of the enzymes, as by their irreversible sorption and unfolding. Various organic or inorganic substances used in biotechnology as solid supports for chromatography or electrophoresis of biopolymers, for enzyme or cell immobilization, as well as for growing bacteria, cells and viruses; such as agarose, polyacrylamide, nylon, gelatin, alginate, carrageenan, cellulose, silica gel, titanium sponge, cross-linked agarose, dextran or polyethylene glycol, and. their combinations and derivatives are suitable (Primrose, S. B. (1987). Modern Biotechnology. Blackwell Scientific Publications, Oxford; Osterman, L. A. (1986). Methods of Protein and Nucleic Acid Research, Vol. 3. Springer-Verlag, New York; Scopes, R. K. (1982). Protein Purification: Principles and Practice. Springer-Verlag, New York; Golubev, V. N., Meteshkin, Yu. V., Kananykhina, E. N., Antonyuk, V. P. and Koshel, M. I. (1989). U.S.S.R. Patent SU 1472505 A1]. When using a new type of the solid matrix, preliminary experiments should be carried out to check whether nucleic acids and/or proteins can be synthesized in the immobilized medium to a detectable level. The choice of a solid matrix also depends on a particular application. For example, temperature-resistant media should be used to carry out PCR. In this case, matrices such as comprised of polyacrylamide, cellulose, polyamide (nylon), or of cross-linked agarose, dextran or polyethylene glycol, are appropriate.

The immobilized medium according to our invention also contains the components of an amplification and/or an expression system comprising the components of a cell-free enzyme system capable of exponential amplification and/or of expression of nucleic acids, respectively. Such cell-free enzyme systems are well known in the art, and are discussed above. Enzymes included in the enzyme systems can be either dissolved in the liquid phase, or be immobilized on the solid matrix [Klibanov, A. M. (1983). Immobilized Enzymes and Cells as Practical Catalysts. Science 219, 722–727].

Figure 1:
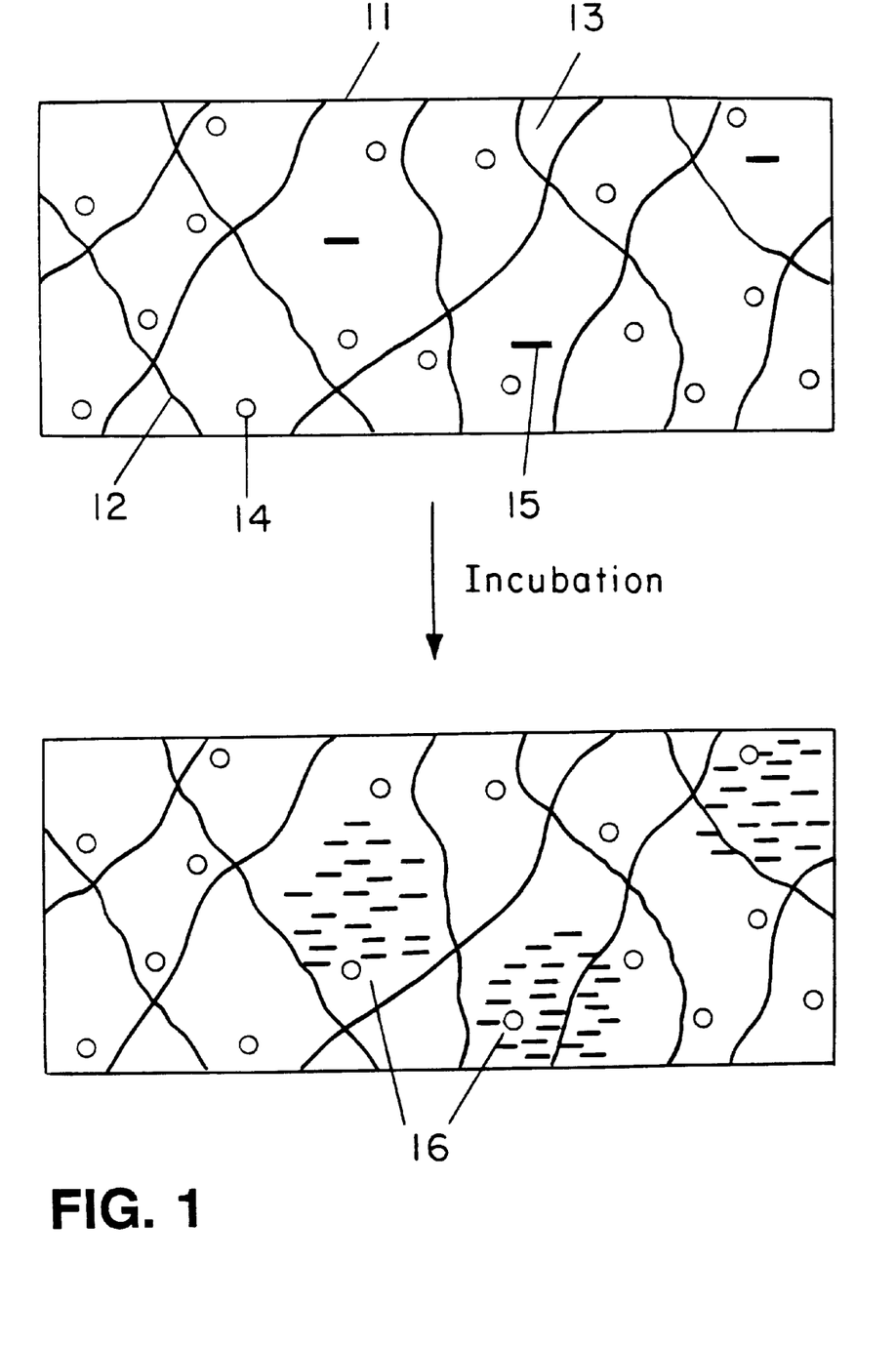
FIG. 1 shows, schematically, growing nucleic acid colonies in an immobilized medium.

During amplification in an immobilized medium, nucleic acids grow as colonies rather than spread throughout the reaction volume, as schematically illustrated in FIG. 1. The upper diagram shows segment 11 of an immobilized medium comprising solid matrix 12, and liquid phase 13 wherein the matrix is immersed and which contains reaction buffer and nucleotide substrates (not shown), enzyme molecules 14 and nucleic acid templates 15. After incubating the immobilized medium for a period of time at a temperature regime allowing nucleic acids to be amplified, nucleic acid colonies 16 form at the locations where the parental nucleic acid templates have been entrapped (the lower diagram). Similarly, during expression of nucleic acids in an immobilized medium, the expression products are accumulated at the locations where the expressed templates have been entrapped.

When carrying out amplification, it is preferred that the solid matrix is capable of reversible interactions with the nucleic acid molecules. Such interactions restrain diffusion of nucleic acids in the liquid phase, resulting in colonies with a smaller size, sharper edges, and higher concentration of nucleic acids. Most hydrophillic matrices are capable of interacting with nucleic acids to some, though different, extent due to hydrogen bonding. This ability can be further increased by chemically modifying the solid matrix with positively charged groups (providing for ionic interactions with phosphate residues in nucleic acids), and/or moderately hydrophobic groups (providing for interactions with purine and pyrimidine rings; care should be taken that the presence of hydrophobic groups does not cause denaturing of the enzymes). At the same time, the interactions should not be too strong, and the modification should not be too extensive, so that the immobilization of the nucleic acids on the solid matrix is readily reversible; otherwise, nucleic acid strands may become unavailable as templates for the amplification reaction. For example, modification of the solid matrix with weak cationic groups, such as secondary or tertiary amino groups (e.g. ethylaminoethyl, or diethylaminoethyl), is appropriate. The solid matrix can also be modified with intercalating dyes such as ethidium or propydium groups [Baidus, A. N., Babaeva, P. V., Remnev, Yu. V., Kolombet, L. V. and borovik, R. V. (1989). U.S.S.R. Patent SU 1230187 A1]. These groups are capable of hydrophobic interactions with the stacked bases of nucleic acids and are positively charged. Moreover, the presence of these groups enables the growing nucleic acid colonies to be detected by fluorescence (see below). Methods of modifying solid matrices with various chemical groups are known in the art, and a variety of modified polymers is commercially available. Many suitable solid matrices and their derivatives compatible with enzymes and nucleic acids are widely used in liquid chromatography of biopolymers [Osterman, L. A. (1986), Scopes, R. K. (1982), supra].

Any mobile liquid outside the immobilized medium should preferably be eliminated, so that nucleic acid or protein molecules cannot be transferred to another location during the reaction. For example, water should not be allowed to condense off the surface of the immobilized medium. At the same time, the immobilized medium should not be allowed to get too dry, as this can result in inactivation of the enzyme(s). Drying up of the immobilized medium during the reaction can be prevented by carrying out the reaction in a properly closed chamber or in a cassette, by wrapping or sealing the medium with a film, or by overlaying the medium with an oil.

It is preferred to suppress the reaction until the medium gets immobilized, especially in the case of an amplification reaction; otherwise the reaction products will be prematurely synthesized and spread throughout the medium. This requirement can easily be met in the case of PCR, as the reaction does not proceed until temperature cycling is started. When carrying out an isothermal reaction, such as 3SR or VRP reaction, or an expression reaction, this can be achieved by either preparing the medium at or close to 0° C. when the reaction is very slow; or keeping the reaction substrates and/or nucleic acids away from the enzyme(s) until the medium is immobilized; or having the reaction substrate(s) in a chemically unavailable "caged" form, which can be decomposed to release the normal substrate(s). An example of caged substrate is a photosensitive derivative of ATP, wherein the γ-phosphate is modified with a 1-(2-nitro)phenylethyl group [Kaplan, J. H., Forbush, B., III, and Hoffman, J. F. (1978). Rapid Photolytic Release of Adenosine 5'-Triphosphate from a Protected Analogue: Utilization by the Na:K Pump of Human Red Blood Cell Ghosts. Biochemistry 17, 1929–1935] that can be converted into ATP by photolysis to initiate the reaction.

Depending on the application, the medium can be shaped into a thick bed, or into a thin layer.

Carrying out a reaction in a thick bed (packed in any suitable container such as a tube, a flask, a column, or a cartridge) can be useful when the purpose of the procedure is mere propagation, of, e.g., cloned nucleic acids. The purpose of employing an immobilized medium in this case is to minimize the interference from the background growth, especially if contaminating nucleic acids are more efficient templates than those to be propagated. This is especially important if an amplification reaction is primer-independent, such as the VRP reaction. carrying out the reaction in an immobilized medium allows the contaminating nucleic acids to be amplified at, and their competition to the growth of the desired nucleic acids be restricted to, limited zones of an immobilized medium where the contaminating templates were originally entrapped.

It is preferred that the thick bed be prepared in such a manner that enzymes (in the examples below understood as together with nucleic acid templates and all other macromolecular reaction components, which is understood in the examples below) and substrates are present in separate zones that are shaped into granules, lamellae, or filaments and surround each other. In this format, the enzymes and substrates are kept apart during medium preparation, and the reaction starts simultaneously throughout the bed volume as the substrates begin to penetrate into the enzyme zones. Examples of such embodiments are the following.

(a) A first solution containing melted agarose and a buffer is mixed at ≈40° C. with enzymes and, while liquid, is dropped into a cold buffer to form beads. Alternatively, enzyme-containing agarose is cast in a bed which is then crushed into small granules. Enzyme-containing beads can also be prepared by soaking a commercially available beaded agarose in an appropriate solution, or by dispersion of an agarose:enzyme solution in an oil, as described for the entrapment of living cells [Nilsson, K., Brodelius, P., and Mosbach, K. (1987). Entrapment of Microbial and Plant Cells in Beaded Polymers. Methods Enzymol. 135, 222–230]. The cold drained granules containing enzyme(s) are then poured into a second agarose solution containing reaction substrates and is pre-cooled but still liquid, and which is then placed on ice to ensure rapid gelling of agarose. (Of course, the reversed format can also be used, i.e. fusion of the granules containing nucleotides into the agarose containing enzyme(s) and template.) The immobilized medium is incubated at 20 to 37° C. to allow the reaction to proceed, and the reaction product are eluted or extracted by an appropriate method known in the art.

(b) The enzyme-containing granules described in (a) are coated with alginate shells by including sodium alginate into the first agarose solution and calcium ions into the buffer whereinto the solution is dropped, or by soaking the already formed granules in a solution containing alginic acid, and then pouring the drained granules into a $Ca^{2+}$-containing buffer. Alginate shells can be further hardened by treating them with polyethylene imine. Bucke, C. (1987). Cell Immobilization in Calcium Alginate. Methods Enzymol. 135, 175–189. The granules can also be coated with kappa-carrageenan [Chibata, I., Tosa, T., Sato, T. and Takata, I. (1987). Immobilization of Cells in Carrageenan. Methods Enzymol. 135, 189–198], or with cellulose nitrate, nylon, and other types of semipermeable membranes [Chang, T. M. S. (1976). Microencapsulation of Enzymes and Biologicals. Methods Enzymol. 44, 201–218]. The reaction is then carried out in the coated granules (capsules) by incubating them in a substrate-containing solution. In contrast to small solutes such as nucleotide substrates, large molecules such as enzymes and nucleic acids can hardly permeate through the shells, so that their loss into the surrounding solution, as well as migration of nucleic acid molecules between the capsules, is substantially prevented. A higher yield of the reaction can be obtained by packing the capsules in a column and continuously washing them with a fresh substrate solution. After completion of the reaction, the shells are dissolved in an appropriate solution (for example, alginate shells can be dissolved by simply chelating $Ca^{2+}$), or the capsules are homogenized to recover the reaction products.

(c) Granules containing enzymes and nucleic acids are prepared by using agarose or another gel-producing polymeric substance modified with positively charged groups, such as diethylaminoethyl groups, and the amplification reaction is carried oat as described for capsules. In this case, nucleic acids and enzymes become captured within the granules due to ionic interactions with the agarose matrix. After the reaction, the synthesized products are eluted from the granules by a buffer with a high concentration (up to 1–2 M) of salt.

(d) To amplify nucleic acids, the enzyme-containing agarose (or another gel-producing) solution can be poured into a hollow-fiber cartridge, so that the solution fills the space either outside or inside the fibers and is solidified there by cooling. The fibers impermeable for large molecules but permeable for nucleotides, such as Diaflo hollow fibers type P10-20 sold by Amicon, Inc. are used. To carry out the amplification reaction, the opposite side of the fiber walls is washed with a solution containing nucleotides. After the reaction, agarose is melted by heating, removed from the cartridge, and nucleic acids are isolated by phenol extraction and/or by ion-exchange chromatography.

In most applications, however, the use of a thin layer of an immobilized medium is preferred. In this format, the growing nucleic acid colonies are arranged in a substantially two-dimensional pattern. This makes it easier to separately observe, analyze and handle individual colonies, and also allows replicas of the colony pattern to be prepared, by, e.g., colony transfer onto a blotting membrane. The replicas can then be used for screening the colonies, transferring them onto another medium or for any other purpose, or can be stored for further use. Thin layers are also useful in expressing nucleic acids, whether it is used for screening colonies or for testing a number of nucleic acid samples, e.g., by spotting the samples on an expressing layer. Small thickness of a layer reduces transversal temperature gradients (that is essential for PCR) and facilitates penetration of substrates (that is essential for the embodiments that use a sandwich format, see below). Preferably, the thickness of a layer should not exceed the colony size which depends mainly on the rate of nucleic acid diffusion, i.e., it should be within several millimeters. The most preferred are very thin layers, as this increases the resolving power of the method and reduces costs. The lower limit of the thickness depends on the mechanical strength of the solid matrix, on the possibility to prevent its drying during manipulation and during the reaction, and on the sensitivity of the method used for detecting the reaction products. In practice, the use of layers with a thickness ranging from 1 mm to 50 μm gives quite satisfactory results. Of course, thicker (e.g., 10 mm) and thinner (down to 1 μm) layers can also be used. When using thicker layers, the enzymes and substrates are preferably entrapped in separate layers that are placed one onto another, and the nucleic acids are introduced between them in order to restrict the reaction to a narrow zone near the interface. Thinner layers should preferably be mounted on a strengthening support, such as a glass, metal, or plastic plate or film.

The choice of a technique for preparing thin layers of immobilized media suitable for nucleic acid amplification and/or expression depends on the properties of a solid matrix, on the temperature conditions of the reaction, on the properties of the enzymes used for the reaction (such as their ability to survive the conditions of matrix formation), and on the format of an immobilized medium used, such as a monolayer or multilayer medium. Monolayer media are convenient to use if all the components of an amplification can be mixed together without allowing the reaction to start until the layer is ready, as in PCR that does not proceed unless temperature cycling is started. Monolayer media can also be used when substrates should be kept away from enzymes until the layer gets solid. In this case, the layer containing enzymes and templates can be prepared and contacted with the substrate solution through a semipermeable membrane, such as a dialysis membrane. A stack of such layers can be used for a large-scale propagation of nucleic acids as an alternative to using a column filled with granules or a hollow-fiber cartridge discussed above.

In many cases a multilayer, or "sandwich", format is preferred. In this case, the enzyme(s) and the substrates of the reaction can be entrapped in separate layers which are contacted. when desired, and the reaction is started as a result of diffusion of substrates into the enzyme layer. A sandwich format can also be preferred even in the cases when keeping substrates away from enzymes during the medium preparation is not necessary, such as in PCR. For example, the second layer can be a blotting membrane, so that transfer of nucleic acids to that membrane can proceed simultaneously with their amplification; or the second layer can contain the components of an expression system and be applied onto a first layer after PCR is completed to screen the PCR colonies by their expression products. In the latter case, a third layer can also be used: this can be a blotting membrane, or a membrane carrying substrates of the enzyme(s) expected to be synthesized in the second layer during the expression reaction. By using a sandwich medium it is also possible to prepare a number of replicas while amplifying nucleic acids (e.g. by employing a medium comprising several blotting membranes stacked one on another), and to supplement the medium with new components at a predetermined reaction time.

Thin layers suitable for nucleic acid amplification and/or expression can be prepared in different ways, such as impregnation of a dry or wet solid matrix with a solution containing enzyme(s) and/or substrates, or entrapment of the enzyme(s) and/or substrates during gelling of a formerly liquid medium.

(a) Entrapment during medium gelling.—Gel-producing solutions, such as those based on agarose, gelatin, or kappa-carrageenan, are mixed with a concentrated enzyme and/or substrate solution, poured onto a flat surface, such as the bottom of a Petri dish, and cooled to form a gel. A more thin and uniform layer without a meniscus can be obtained by casting the gel between two flat spaced surfaces. Kappa-carrageenan gel can be further strengthened by soaking the layer in a potassium salt [Chibata et al. (1987), supra].

To prepare a polyacrylamide-based layer, or a layer based on a composite agarose/polyacrylamide gel, enzyme(s) and/or substrates are added to an acrylamide:N,N'-methylene bisacrylamide monomer-containing solution prior to the addition of a polymerization catalyst, and polymerization is carried out as described for enzyme entrapment in polyacrylic gels [O'Driscoll, K. F. (1976). Techniques of Enzyme Entrapment in Gels. Methods Enzymol. 44, 169–183]. The gel is cast between two spaced flat surfaces. Enzymes and/or substrates can also be entrapped during polymerization of photo-cross-linkable polyethyleneglycol resins, a method industrially used for production of the sheets carrying immobilized living cells [Nojima, S. and Yamada, T. (1987). Large-scale Production of Photo-cross-linkable Resin-immobilized Yeast and Its Application to Industrial Ethanol Production. Methods Enzymol. 136, 380–394].

(b) Enzyme and/or substrate entrapment by impregnating a pre-formed solid matrix.—Fibrous thin layers, such as those based on cellulose or nylon, or porous layer such as based on silica gel or titanium sponge, are easy to prepare by soaking dry sheets, membranes or plates with a solution containing all or some of the reaction components. Care should be taken that the solid layer does not contain soluble substances that can be noxious for enzyme(s), e.g. surfactants that could have been used during its manufacturing; in the case of any doubt, it should be pre-washed and dried. After soaking, any excessive liquid is drained, and the layer is immediately placed under conditions that prevent further drying.

Impregnation of pre-cast gels with enzymes and/or substrates can be a choice when the conditions of gel preparation are too strong for these labile biological substances. For example, agarose gels melt at high temperature, and therefore they are not suitable for use in PCR. Agarose can be cross-linked, e.g., with epichlorohydrine or 2,3-dibrobopropanol to increase its temperature resistance so that it can be heated up to 120° C. without melting. Porath, J., Janson, J.-C. and Låås, T. (1971). Agar Derivatives for Chromatography, Electrophoresis, and Gel-bound Enzymes. I. Desulphated and Reduced Cross-linked Agar and Agarose in Spherical Bead Form. J. Chromatogr. 60, 167–177; Osterman, L. A. (1986). Methods of Protein and Nucleic Acid Research, Vol. 3. Springer-Verlag, New York. Similarly, rather rigid and temperature-resistant gels can be obtained by cross-linking dextrans with epichlorohydrine or with N,N'-methylene bisacrylamide [Flodin, P. (1962). Dextran Gels and Their Applications in Gel Filtration, Dissertation, AB Pharmacia, Uppsala, Sweden; Osterman (1986), supra]. However, in most cases cross-linking occurs under conditions that cannot be tolerated by the enzymes and substrates of the amplification or expression reaction. Therefore, a layer is pre-formed without enzyme(s) or substrates, washed, and soaked in absolution containing enzyme(s) and/or substrates. Prior to soaking, the layer can be lyophilized or dried in vacuo after water has been displaced with ethanol or methanol. Similarly, polyacrylamide or polyacrylamide:agarose gels can also be pre-cast, washed, and then impregnated with enzyme(s) and/or substrates.

Nucleic acids intended for amplification and/or expression, should be introduced into the liquid phase of a layer by including them into the enzyme and/or substrate solution prior to its immobilization, or by spreading or spotting them on the surface of a layer or on the interface between layers. It is preferred that a layer is formed and nucleic acids are introduced therein under conditions that suppress the reaction, and then it is put under conditions that promote the reaction (such as increased temperature, temperature cycling, or illumination, see above). In the case of isothermal reactions, the enzymes and substrates are preferably entrapped into separate layers, and the layers are contacted at a pre-determined time to initiate the reaction. Reaction is carried out during a pre-determined time period. In an amplification reaction, a sufficient number of replication rounds should occur to produce detectable colonies. At least $10^6$ copies of a nucleic acid should be generated in each colony, requiring 20 rounds of replication to occur provided that each round results in doubling of the number of templates, which is about the lower limit of the currently existing methods for detecting nucleic acids [Landegren, U., Kaiser, R., Caskey, C. T., and Hood, L. (1988). DNA Diagnostics—Molecular Techniques and Automation. Science 242, 229–237].

After incubation, nucleic acid colonies can be detected by a variety of methods, for example, by staining the layer with intercalating dyes such as ethidium bromide or propydium iodide, by autoradiography of a blotting membrane onto which the nucleic acids have been transferred provided that amplification occurred in the presence of a substrate labeled with a radioisotope, or by a variety of non-isotopic methods employing nucleic acid or substrate modification with a non-isotopic reporter group, such as biotin or digoxigenin. Colonies can also be screened for possessing a particular trait, such as carrying a particular nucleic acid sequence (by hybridizing the nucleic acids with specific probes directly in a growth layer or after their transfer to a blotting membrane), or carrying a gene encoding a particular protein (by in vitro expression of the nucleic acids).

If the transfer onto a blotting membrane is chosen, it is preferred that the membrane is applied to the growth layer before amplification, so that nucleic acids are continuously transferred as they are synthesized. Hybridization can be carried out with chemically synthesized oligonucleotide probes, or with nucleic acid probes synthesized enzymatically, e.g., in PCR or in a transcription reaction. The probes can be radioactively labeled and hybrids can be detected by autoradiography. Sambrook, J., Fritsch, E. F. and Maniatis, T. (1989). Molecular Cloning: A Laboratory Manual, 2nd edition. Cold Spring Harbor Laboratory Press, Cold Spring Harbor, N.Y. Methods not employing radioactive isotopes, such as using fluorescent labels and those using coupled peroxidase and phosphatase reactions, are also appropriate [Forster, A. C., McInnes, J. L., Skingle, D. C. and Symons, R. H. (1985). Non-radioactive Hybridization Probes Prepared by the Chemical Labelling of DNA and RNA with a Novel Reagent, Photobiotin. Nucleic Acids Res. 13, 745–761; Agrawal, S., Christodoulou, C. and Gait, M. J. (1986). Efficient Methods for Attaching Non-radioactive Labels to the 5' Ends of Synthetic Oligodeoxyribonucleotides. Nucleic Acids Res. 14, 6227–6245; Landegren, U., Kaiser, R., Caskey, C. T. and Hood, L. (1988). DNA Diagnostics—Molecular Techniques and Automation. Science 242, 229–237; Tizard, R., Cate, R. L., Ramachandran, K. L., Wysk, M., Voyta, J. C., Murphy, O. J. and Bronstein, I. (1990). Imaging of DNA Sequences with Chemiluminescence. Proc. Natl. Acad. Sci. U.S.A. 87, 4514–4518; Holtke, H. J., Sagner, G., Kessler, C. and Schmitz, G. (1992). Sensitive Chemiluminescent Detection of Digoxigenin-labeled Nucleic Acids: A Fast and Simple Protocol and Its Applications. BioTechniques 12, 104–112].

Expression of nucleic acids for screening purposes can be done in a liquid reaction medium, but preferably it is carried out in an immobilized medium shaped into at least one thin layer according to our invention. In this format, many colonies can be screened in parallel in one reaction. Expressing nucleic acids in an immobilized medium results in the expression products being accumulated within the zones where the nucleic acid templates are entrapped. When employing an isothermal nucleic acid amplification system such as VRP or 3SR reaction, the components of an appropriate cell-free expression system can be included in the layer(s) that contains the components of the amplification system. When PCR is used for DNA amplification, the expression system can be present in the same medium but in a different layer(s) cast atop the amplification layer(s) after PCR is completed, or it can be present in a different medium. In the latter case, DNA colonies are transferred to the expression medium, e.g., by using a blotting membrane. Expression in an immobilized medium is also useful for testing en masse many nucleic acid samples obtained by any different method, e.g., by spotting the samples on a layer containing the components of an appropriate expression system.

For expression, nucleic acids can be provided in the form of mRNA (as they are synthesized in 3SR or in VRP reactions), and translated into proteins in a medium containing a cell-free translation system [Anderson, C. W., Straus, J. W. and Dudock, B. S. (1983). Preparation of a Cell-free Protein-synthesizing System from Wheat Germ. Methods Enzymol. 101, 635–644; Chambliss, G. H., Henkin, T. M. and Leventhal, J. M. (1983). Bacterial in vitro Protein-synthesis Systems. Methods Enzymol. 101, 598–605; Merrick, W. C. (1983). Translation of Exogenous mRNAs in Reticulocyte Lysates. Methods Enzymol. 101, 606–615]. If nucleic acids are provided in the form of DNA (as they are synthesized in PCR), the expression is carried out in a medium containing a coupled transcription/translation system [Chen, H.-Z. and Zubay, G. (1983). Prokaryotic Coupled Transcription-translation. Methods Enzymol. 101, 674–690; Bujard, H., Gentz, R., Lanzer, M., Stueber, D., Mueller, M., Ibrahimi, I., Haeuptle, M.-T. and Dobberstein, B. (1987). A T5 Promoter-based Transcription-translation System for the Analysis of Proteins in vitro and in vivo. Methods Enzymol. 155, 416–433; Tymms, M. J. and McInnes, B. (1988). Efficient in vitro Expression of Interferon Analogs Using SP6 Polymerase and Rabbit Reticulocyte Lysate. Gene Anal. Tech. 5, 9–15; Baranov, V. I., Morozov, I. Yu., Ortlepp, S. A. and Spirin, A. S. (1989). Gene Expression in a Cell-free System on the Preparative Scale, Gene 84, 463–466; Lesley, S. A., Brow, M. A. and Burgess, R. R. (1991). Use of in vitro Protein Synthesis from Polymerase Chain Reaction-generated Templates to Study Interaction of *Escherichia coli* Transcription Factors with Core RNA Polymerase and for Epitope Mapping of Monoclonal Antibodies. J. Biol. Chem. 266, 2632–2638].

The synthesized polypeptides can be identified in situ or on a replica by a variety of known methods, such as by an immunoassay, or by their ability to perform specific enzymatic reactions or to bind a specific ligand.

Our invention also includes applications of the method of amplification of nucleic acids in immobilized media for diagnostics and cloning of nucleic acids in vitro.

Our invention allows even solitary molecules of specific nucleic acids to be detected in a sample, including samples containing large amounts of unrelated nucleic acids, thereby providing for extremely sensitive diagnostics of clinical, agricultural, and environmental conditions. The sample can be taken from a variety of sources, such as a biological fluid or tissue, raw water, and air, and it can be analyzed for the presence of particular viruses, bacteria and other microorganisms, as well as their remains, and for the presence of particular genes in higher organisms, such as mutant genes or oncogenes. The procedure comprises (i) obtaining a sample that possibly contains nucleic acids of interest (the target); (ii) exposing the target by an appropriate lytic treatment, such as phenol extraction or lysis with detergents or guanidine isothiocyanate; (iii) removing (or diluting) the lytic agent and preferably any irrelevant material that can interfere with the assay, such as cellular debris or dust; (iv) amplification of the target, its segment, or a replicatable reporter nucleic acid generated in a target-dependent reaction [see Kramer, F. R., and Lizardi, P. M. (1989). Replicatable RNA Reporters. Nature 339, 401–402; and Example 4 below] in a thin layer of an immobilized medium containing an appropriate cell-free enzyme system capable of exponential amplification of said target, its segment, or reporter molecules to produce detectable colonies; and (v) detecting target-related colonies (the positive colonies) by their ability to bind specific probes, such as oligonucleotide probes. Even if a single positive colony appears among hundreds or thousands of target-unrelated (negative) colonies, it will be reliably detected by this method. Quantitative assays are also possible with this technique. For this purpose, one should prepare serial dilutions of the target sample and count the number of colonies obtained with each dilution. The technique also allows to carry out the assay of a number of different targets simultaneously. In this case, step (v) of the procedure is carried out by employing the corresponding number of different specific probes. The colonies can be screened with individual probes consecutively or in parallel (employing the replicas of the colony pattern prepared on blotting membranes). Alternatively, several probes can be tested together, provided that each of them is differently labeled.

Because of the extreme sensitivity of the method, it is essential to prevent any contamination of the samples by exogenous targets prior to the amplification step. Therefore, the steps preceding nucleic acids amplification and those following it (such as colony screening) should preferably be carried out in different laboratories. The screening laboratory should be of a restricted access and equipped according to the biohazard level 3 standards or the like, and after analysis the colonies and replicas should be properly deactivated under conditions destroying nucleic acids. The amplification step should preferably be carried out in hermetic cassettes which are sealed in the laboratory wherein the samples are prepared and are opened in the screening laboratory. It is also useful to inactivate the amplified nucleic acids before opening the cassette, e.g., by inclusion into the growth layer reagents like photoactivatable isopsoralen derivatives which do not interfere with the amplification reaction and after illumination following the amplification reaction form covalent adducts with pyrimidine bases resulting in the loss of the ability of nucleic acids to serve as templates for subsequent amplifications. At the same time, the modified nucleic acids retain the ability of specific hybridization with oligonucleotide probes [Cimino, G. D., Metchette, K. C., Tessman, J. W., Hearst, J. E. and Isaacs, S. T. (1991). Post-PCR Sterilization: a Method to Control Carryover Contamination for the Polymerase Chain Reaction. Nucleic Acids Res. 19, 99–107; Isaacs, S. T., Tessman, J. W., Metchette, K. C., Hearst, J. E. and Cimino, G. D. (1991) Post-PCR Sterilization: Development and Application to an HIV-1 Diagnostic Assay. Nucleic Acids Res. 19, 109–116]. In this case the cassette where the amplification reaction is carried out is made of a UV-transparent plastic and exposed to a 300–400 nm light before opening. It is also important to check the reliability of the assays by running control samples, such as those containing no added target (to monitor contaminations) and those containing a measured amount of a target (to assess the assay efficiency).

The procedure for the in vitro cloning of nucleic acids essentially parallels the diagnostic procedure. After nucleic acid colonies have grown, they are screened for possessing particular traits either by hybridizing the nucleic acids with specific probes, or by their ability to synthesize particular proteins. The clones of interest can be picked up and amplified to a desired amount as described above. The in vitro cloning has all the same applications as does the cloning in vivo [Sambrook et al. (1989), supra], and it has advantages over the in vivo cloning as it is faster, it allows any arbitrary nucleic acid to be cloned without restrains from the cellular control, and it allows pure genes to be directly obtained free from contaminating by chromosomal DNA or cellular RNA. The cloned nucleic acids can be used for a variety of purposes, such as for transformation of cells, for the use in antisense therapy, or for the use as templates in cell-free protein synthesis bioreactors [Spirin, A. S. (1992). Cell-free Protein Synthesis Bioreactor. In Frontiers in Bioprocessing II, ed. by P. Todd, S. K. Sikdar and M. Bier. American Chemical Society, Washington, D.C., pp. 31–43].

The invention will now be described in greater detail by way of examples.

EXAMPLE 1

Growing RNA Colonies in VRP Reaction

In this example, the technique of RNA amplification in thin layers of immobilized media is illustrated by the amplification of RQ RNAs that are naturally occurring Qβ replicase templates. Qβ replicase is the most efficient of known viral RNA polymerases. It can easily be purified to homogeneity on a preparative scale, can be stored for a long time without the loss of activity, and is stable during the reaction in vitro, allowing multiple rounds of replication to be performed in a single incubation [Blumenthal, T. (1979). Qβ RNA Replicase and Protein Synthesis Elongation Factors EF-Tu and EF-Ts. Methods Enzymol. 60, 628–638].

Agarose powder (ultra-low gelling temperature agarose type IX, Sigma Chemical Company) is melted by heating in an autoclaved buffer [80 mM Tris-HCl pH 7.8, 12 mM $MgCl_2$, 1 mM Tris-EDTA (ethylenediamine tetraacetic acid), 20% glycerol], cooled to ≈40° C., and thoroughly mixed by vortexing with a concentrated solution of Qβ replicase purified as described [Blumenthal (1979), supra]. Final concentrations of agarose and Qβ replicase are 2% and 35 μg/ml, respectively. A sandwich medium is then prepared in one of the two following formats (when required, an appropriately diluted RNA template is introduced into a substrate layer, or is spread on the interface between the enzyme and substrate layers).

Figure 2A:
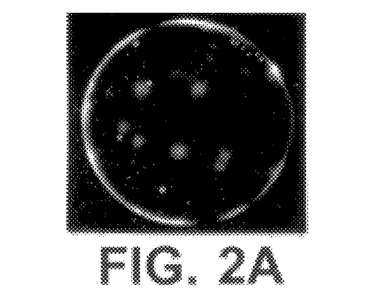
FIG. 2 shows RNA colonies grown in thin layers containing the Qβ replicase enzyme system.
Figure 2B:
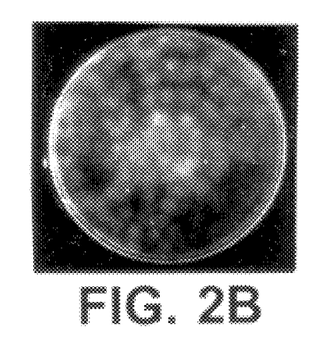
Figure 2C:
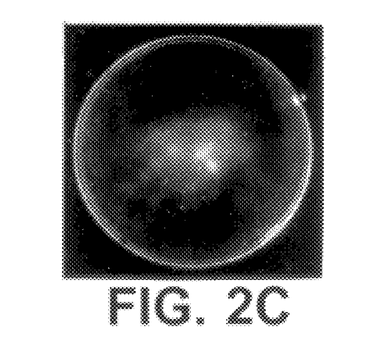

(a) 1,5 ml of this solution is poured onto a layer of 1% agarose (SeaKem, FMC BioProducts) containing substrates (1 mM each of ATP, GTP, CTP and UTP) that has been prepared in a 35-mm plastic Petri dish. RNA amplification is carried out by incubating the dish at room temperature for 60 min. RNA colonies are visualized by staining with ethidium bromide, as shown in FIGS. 2A and 2B. FIG. 2A shows a few "spontaneously" grown RNA colonies that are observed when the upper (enzyme-containing) layer is cast immediately after the substrate layer has solidified. FIG. 2B shows a number of RNA colonies grown as a result of exposure of the substrate to laboratory air for 1 hour prior to the casting of the enzyme layer. This experiment demonstrates the effectiveness of the invented technique in preventing the background growth to spread over the reaction volume, and the potential danger from exogenous contaminations if the exponential amplification of nucleic acids is carried out in a liquid media. The stain can also be included in the substrate layer; in this case, the colony can be continuously monitored as they are growing (FIG. 2C).

Figure 2D:
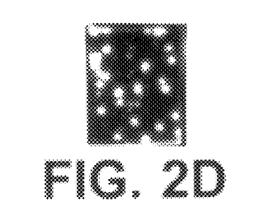
Figure 2E:
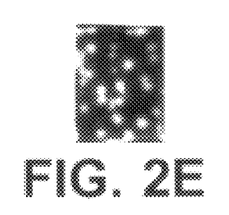

(b) Alternatively, 0.13 ml of the enzyme:agarose solution is cast between a glass cover slip used in microscopy and a larger surface which are spaced by 0.4 mm. After gelling of agarose the cover slip is removed and agarose is overlaid with a sheet of a nylon membrane that has been moistened with a substrate solution (4 mM each of ATP, GTP, CTP, and UTP) and then dried. To visualize RNA colonies by autoradiography, an [$\alpha$-$^{32}$P]-labeled nucleoside triphosphate is added to the substrate solution. After incubating the layers at room temperature or at 37° C. for 20 to 30 min, the membrane is removed from agarose and immersed into an ice-cold fixing solution (such as 3% phosphoric acid, 50 mM $Na_2P_2O_7$, 1 mM EDTA). A second dry nylon membrane (without substrates) can be applied to the agarose layer to prepare a replica and fixed as described above. After washing the membranes to remove unincorporated nucleotides, they are exposed to an X-ray film to visualize colonies. FIG. 2D shows RNA colonies detected with the radioactive label on the original (substrate) nylon membrane, and FIG. 2E shows RNA colonies detected on the second (replica) membrane. It is seen that colonies in FIGS. 2D and 2E are much less diffuse than in FIGS. 2A to 2C. The difference is explained by the presence in the nylon membranes used of positively charged and hydrophobic groups capable of binding RNA molecules. If no labeled substrate has been used, RNA colonies can be detected by staining the agarose layer with ethidium bromide or propydium iodide, or by hybridizing the membrane(s) with specific probes as described below.

For hybridization, the membrane is soaked in a denaturing solution (6% formaldehyde, 50% formamide, 50 mM sodium phosphate buffer pH 7.0, 1 mM EDTA) for 5 min at 65° C. Then RNA is cross-linked to the membrane by ultraviolet light and the membrane is hybridized with a radioactively labeled probe by incubation in a sealed bag between sheets of Whatman 3MM filter paper [Jones, R. W., and Jones, M. J. (1992). Simplified Filter Paper Sandwich Blot Provides Rapid, Background-free Northern Blots. BioTechniques 12, 685–688]. Hybridization temperature is preselected according to Bodkin and Knudson [Bodkin, D. K. and Knudson, D. L. (1985). Sequence Relatedness of Palyam Virus Genes to Cognates of the Palyam Serogroup Viruses by RNA-RNA Blot Hybridization. Virology 143, 55–62], and is optimized for a given probe in preliminary experiments. After hybridization, the membrane is washed from the unhybridized probe and exposed to an X-ray film. To hybridize the membrane with another probe, the first probe is stripped off the membrane by boiling in 0.1% SDS solution [Virca, G. D., Northemann, W., Shiels, B. R., Widera, G. and Broome, S. (1990). Simplified Northern Blot Hybridization Using 5% Sodium Dodecyl Sulfate. BioTechniques 8, 370–371].

Figure 2F:
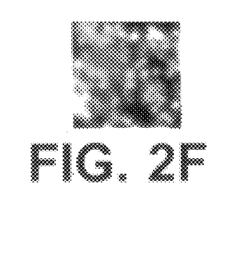
Figure 2G:
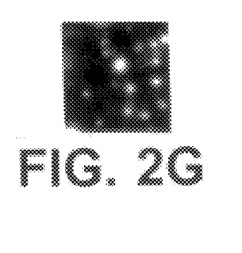

FIGS. 2F and 2G show the results of consecutive hybridizations of the same filter with the probes targeted against RQ87-3 and RQ135-1 RNAs, respectively. These RNAs have been introduced into the substrate layer in the amount of approx. 100–200 copies each. The probes used are [$\alpha$-$^{32}$P] CTP-labeled run-off transcripts prepared by employing T7 RNA polymerase and a plasmid carrying RQ87-3 or RQ135-1 cDNA under the T7 RNA polymerase promoter, essentially as described by Noren et al. [Noren, C. J., Anthony-Cahill, S. J., Suich, D. J., Noren, K. A., Griffith, M. C. and Schultz, P. G. (1990). In vitro Suppression of an Amber Mutation by a Chemically Aminoacylated Transfer RNA Prepared by Runoff Transcription. Nucleic Acids Res. 18, 83–88]. This experiment demonstrates that different colonies contain different RQ RNA species and that the number of colonies approximates the number of introduced template molecules. Thus, true cloning of RNA takes place.

EXAMPLE 2

Growing Nucleic Acid Colonies in Isothermal 3SR Reaction

A low-gelling temperature agarose is melted in a reaction buffer as described in Example 1, and cooled to 40° C. Then it is mixed with AMV reverse transcriptase, T7 RNA polymerase, RNase H, and a template:two primer mixture (pre-heated at 65° C. in the reaction buffer with $Mg^{2+}$ and spermidine omitted) and the enzyme layer is cast as described in Example 1(b). The template can be RNA, DNA, or a mixture thereof; one of the two primers comprises a sequence that is complementary to the 3' terminal sequence of a template strand and the other primer comprises a sequence that is complementary to the 3' terminal sequence of the strand complement, the two primers also containing at the 5' end the T7 RNA polymerase promoter sequence and the preferred transcriptional initiation site (GGGA). The layer is overlaid with a nylon membrane soaked with the reaction buffer containing 4 mM each of dATP, dGTP, dCTP, and dTTP, and 16 mM each of ATP, GTP, CTP, and UTP. The reaction buffer, enzyme and primer concentrations and the amplification reaction conditions are as described by Guatelli et al. [Guatelli, J. C., Whitfield, K. M., Kwoh, D. Y., Barringer, K. J., Richman, D. D. and Gingeras, T. R. (1990). Isothermal, in vitro Amplification of Nucleic Acids by a Multienzyme Reaction Modeled after Retroviral Replication. Proc. Natl. Acad. Sci. U.S.A. 87, 1874–1878]. Nucleic acid colonies are detected by hybridizing the membrane with a probe that is complementary to an internal region of the target template, essentially as described in Example 1(b). Non-radioisotopic detection methods (see above) can also be used.

EXAMPLE 3

Growing Nucleic Acid Colonies in PCR

All reaction components, including buffer, a thermostable DNA polymerase such as *Thermus aquaticus* DNA polymerase, DNA sample, primers, and substrates are mixed with a degassed acrylamide: N,N'-methylene bisacrylamide solution, and catalysts of acrylamide polymerization [ammonium persulphate and N,N,N',N'-tetrametyl ethylene diamine (TEMED)]. A 0.2–0.4 mm-thick gel layer is then cast between two glass plates, one of which having been treated with a bind silane, and the other with a repel silane. After completion-of polymerization, the plate treated with repel silane is removed, the gel is overlaid with a nylon blotting membrane moistened with the reaction buffer, wrapped with a thermostable film, and put onto a thermostating plate with the attached glass plate facing up. To ensure proper heat exchange with the thermostating plate, a thin layer of a mineral oil is placed between the plate surface and the gel-wrapping film. Amplification reaction occurs when temperature of the thermostating plate is cycled (at least 20 cycles are carried out). This is done by employing a temperature-controlling device that is connected through water pipes with the thermostating plate, and that uses three [Torgensen, H., Blaas, D. and Skern, T. (1989). Low Cost Apparatus for Primer-directed DNA Amplification Using *Thermus aquaticus*-DNA Polymerase. Analyt. Biochem. 176, 33–35) or two water baths with different temperature [Weier, H. U. and Gray, J. W. (1988). A Programmable System to Perform the Polymerase Chain Reaction. DNA 7, 44–47]. Commercially available PCR temperature cyclers can also be used after the heating block is modified to accommodate the gel plate. The reaction components, their concentrations, and conditions of PCR are as described by Saiki et al. [Saiki, R. K., Gelfand, D. H., Stoffel, S., Scharf, S. J., Higuchi, R., Horn, G. T., Mullis, K. B. and Erlich, H. A. (1988). Primer-directed Enzymatic Amplification of DNA with a Thermostable DNA Polymerase. Science 239, 487–491]. After completion of PCR, DNA colonies are detected on the nylon membrane by autoradiography (if one of the reaction substrates is radioactively labelled), or by hybridization with a specific probe directed against an internal region of the target DNA as described above.

If RNA rather than DNA is provided, it is first converted into cDNA with a reverse transcriptase [Sambrook, J., Fritsch, E. F., and Maniatis, T. (1989). Molecular Cloning: A Laboratory Manual, 2nd edition. Cold Spring Harbor Laboratory Press, Cold Spring Harbor, N.Y.]. Alternatively, PCR is carried out with *Thermus thermophilus* DNA polymerase, which displays both the DNA polymerase (in a $Mg^{2+}$-containing buffer) and the reverse transcriptase (in a $Mn^{2+}$-containing buffer) activities. In this case, the cDNA synthesis step is carried out before casting the gel. The reaction components and conditions are those described by Myers and Gelfand [Myers, T. W., and Gelfand, D. H. (1991). Reverse Transcription and DNA Amplification by a *Thermus thermophilus* DNA Polymerase. Biochemistry 30, 7661–7666].

EXAMPLE 4

Application of the Method for Amplification of Nucleic Acids in Immobilized Media for Diagnostics In this example, a procedure based on the use of the VRP enzyme system is given, as it is the most elaborated requiring a target-dependent synthesis of a replicatable reporter as proposed by Kramer and Lizardi [Kramer, F. R., and Lizardi, P. M. (1989). Replicatable RNA Reporters. Nature 339, 401–402]. Procedures that employ PCR or 3SR reaction mainly differ from that described in this example in that they do not require the synthesis of a replicatable reporter; rather, the specific amplification of a fragment of a target molecule is controlled by at least two primers directed against the target; the colonies formed by the amplified fragments are identified by hybridizing with labeled probes that are complementary to internal regions of the fragments.

A sample (e.g., a patient's blood sample containing approximately $5 \times 10^6$ cells) is treated with 5 M guanidine isothiocyanate solution, that results in the lysis of cells, denaturing of proteins (including nucleases), and release from cellular debris and denaturation of RNA and DNA [Pellegrino, M. G., Lewin, M. Meyer, W. A., III, Lanciotti, R. S., Bhaduri-Hauck, L., Volsky, D. J., Sakai, K., Folks, T. M. and Gillespie, D. (1987). A Sensitive Solution Hybridization Technique for Detecting RNA in Cells: Application to HIV in Blood Cells. BioTechniques 5, 452–459]. After the guanidine isothiocyanate concentration is adjusted to 2.5 M, the target molecules are captured with probes that are comprised of a sequence that is complementary to the target strand (at a location different from where the reporter probes bind, see below) and a poly(A) tail that enables the capture probe to hybridize to the oligo(dT) covalently linked to the surface of magnetic beads [Morrissey, D. V., Lombardo, M., Eldredge, J. K., Kearney, K. R., Grody, E. P. and Collins, M. L. (1989). Nucleic Acid Hybridization Assays Employing dA-tailed Capture Probes. I. Multiple Capture Methods. Anal. Biochem. 181, 345–359]. After washing the beads, the target molecules are released into solution by heating in a low-salt buffer and used as templates for generation of a replicatable reporter from binary probes by one of the following schemes.

Figure 3A:
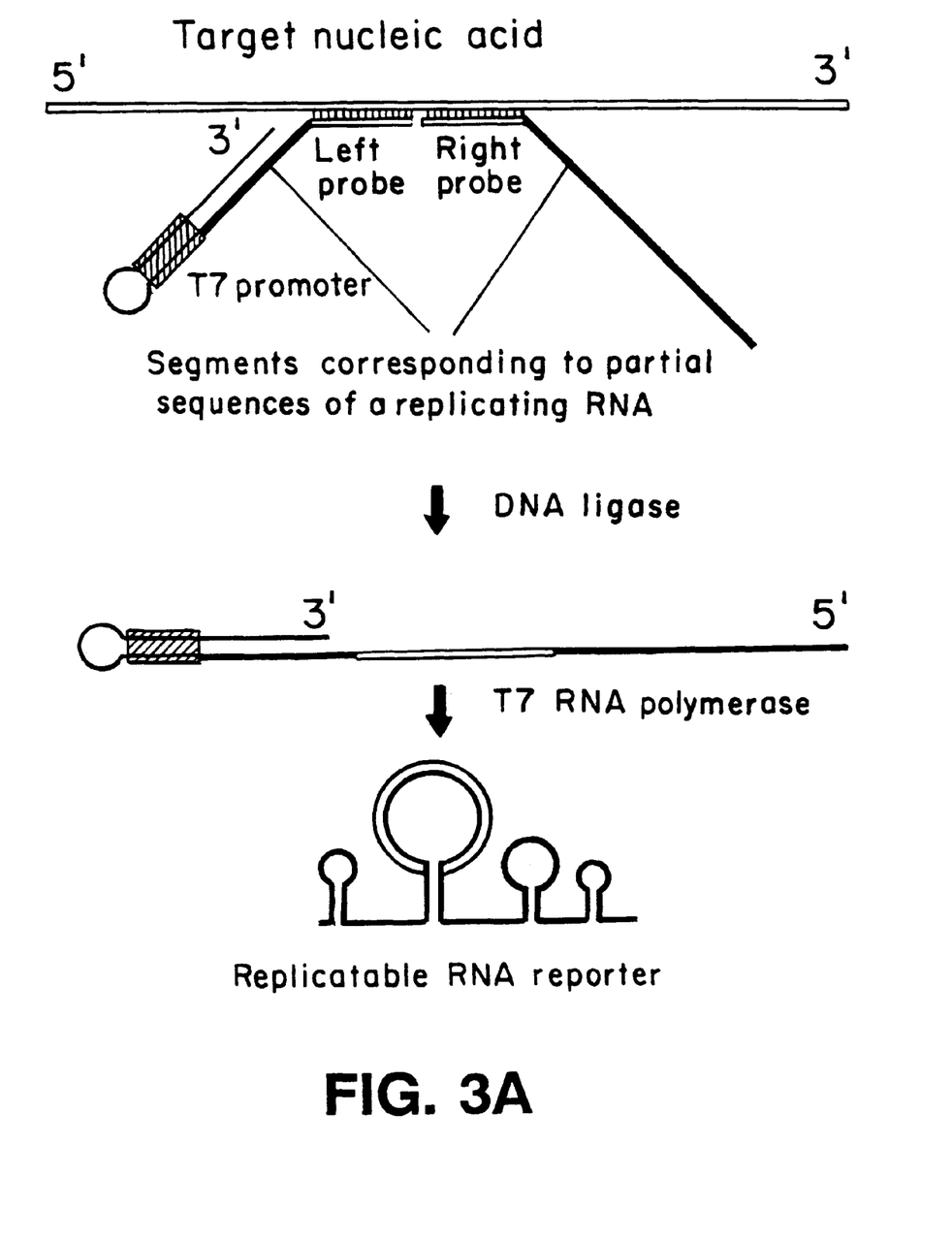
FIG. 3 shows, schematically, a target-dependent formation of replicatable RNA reporters.

(a) Binary probes are converted into a replicatable molecule through a target-directed ligation [Landegren, U., Kaiser, R., Sanders, J. and Hood, L. (1988). A ligase-mediated Gene Detection Technique. Science 241, 1077–1080], as illustrated in FIG. 3A. The two probes are single-stranded DNAs that contain at their ligating ends the sequences that are complementary to adjacent segments of a target sequence (e.g., mRNA of HIV-1 virus). The rest of the probes corresponds to two partial sequences of an efficiently replicating RNA, each of which is incapable of replication by a VRP such as Qβ replicase, but which together give rise to an efficient VRP template if joined into one molecule and transcribed into RNA. The 3'-terminal sequence of one of the two probes comprises a double-stranded T7 promoter to allow transcription of the ligated probes with T7 RNA polymerase. The two probes are hybridized with the isolated target and the hybrid is incubated with DNA ligase to generate a full-length DNA template for the synthesis of a replicatable RNA reporter by subsequent transcription. The ligation of the probes is only possible when both probes are simultaneously hybridized to the same target molecule. The transcript will consist of a recombinant replicating RNA sequence carrying an insert corresponding to a segment of the target. The examples of efficient Qβ replicase templates whose sequences can be used for constructing such probes are MDV-1 RNA [Lizardi, P. M., Guerra, C. E., Lomeli, H., Tussie-Luna, I. and Kramer, F. R. (1988). Exponential Amplification of Recombinant-RNA Hybridization Probes. Bio/Technology 6, 1197–1202] and RQ135 RNA [Munishkin, A. V., Voronin, L. A., Ugarov, V. I., Bondareva, L. A., Chetverina, H. V. and Chetverin, A. B. (1991). Efficient Templates for Qβ Replicase are Formed by Recombination from Heterologous Sequences. J. Mol. Biol. 221, 463–472].

Figure 3B:
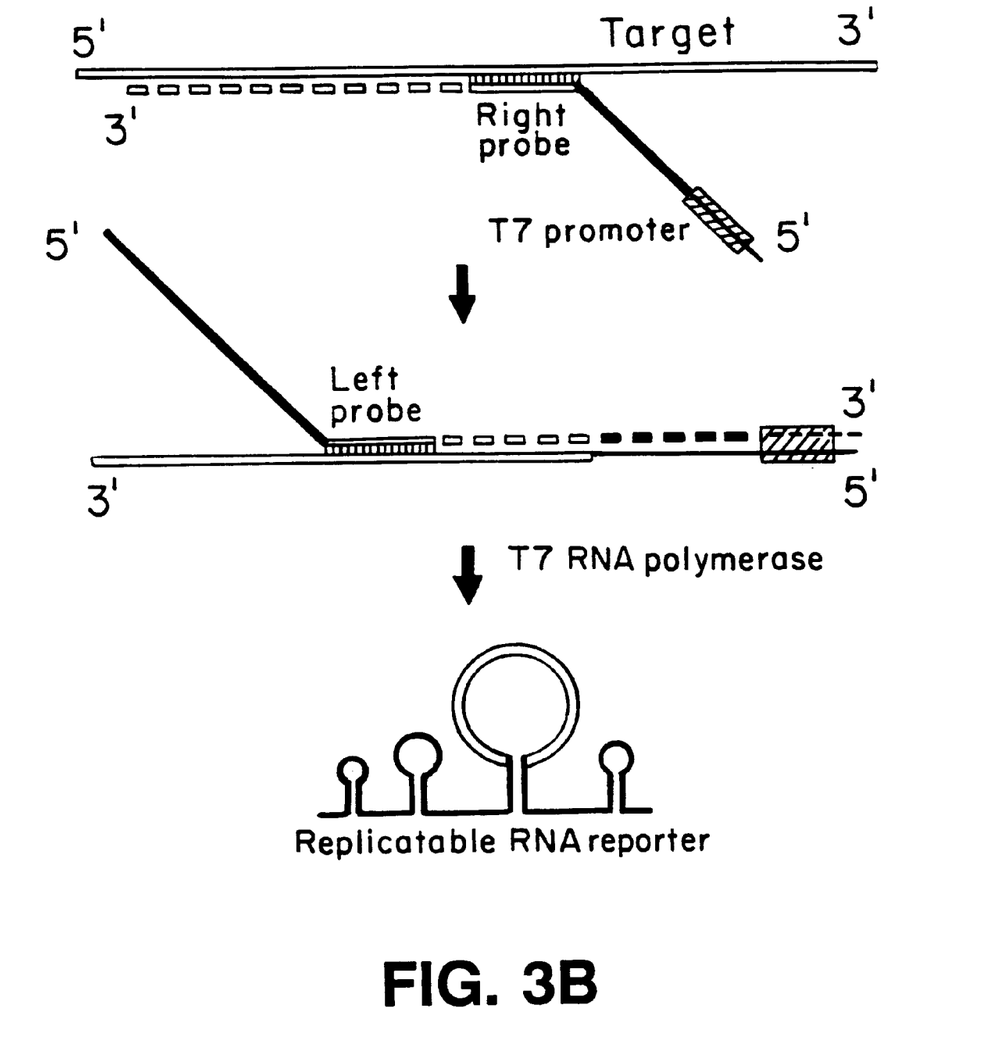

(b) The second scheme is similar to the first one, except that the target-directed probe extension with a DNA polymerase, rather than probe ligation, is used for the generation of a DNA template for the synthesis of a replicatable RNA reporter [Kramer and Lizardi (1989), supra], as illustrated in FIG. 3B. In this case, one of the probes has on its end a segment that hybridizes to a target molecule, while the other probe has a segment that hybridizes to the target's complementary copy. The first probe (upper diagram) contains a T7 RNA polymerase promoter sequence, a template encoding a segment of a replicating RNA, and the first probe sequence. After this probe is hybridized to a target, it serves as a primer for its own extension with an appropriate DNA polymerase utilizing the target molecule as a template. The best choice is the DNA polymerase from *Thermus thermophilus* [Myers and Gelfand (1991), supra], which can efficiently copy RNA as well as DNA, thus allowing the probe to be extended on both the RNA and DNA targets. The extended sequence includes a copy of the target region (dashed line). The extended first probe is then released from the target, permitting its hybridization to a second probe (middle diagram) that contains the second probe sequence and a template encoding the remainder of the replicating RNA. The second probe serves as a primer for its own extension, utilizing the extended first probe as a template. A functional double-stranded T7 promoter and a full-length template DNA encoding a recombinant replicating RNA can be generated only if both probes hybridize to their intended targets. Subsequent incubation of this DNA with T7 RNA polymerase will result in the synthesis of a recombinant replicatable RNA reporter (lower diagram).

After synthesis of a full-length reporter DNA by one of the above schemes, different dilutions of the sample are introduced into the substrate-containing nylon membrane [see Example 1(b)] or spread on the interface between the membrane and the agarose layer. In addition to a VRP as described in Example 1, the agarose layer contains T7 RNA polymerase that synthesizes RNA reporter molecules on DNA templates, as well as other components of the transcription system [Milligan, J. F., Groebe, D. R., Witherell, G. W. and Uhlenbeck, O. C. (1987). Oligoribonucleotide Synthesis Using T7 RNA Polymerase and Synthetic DNA Templates. Nucleic Acids Res. 15, 8783–8798]. The RNA transcripts are synthesized at the locations where the DNA templates have been trapped and then are exponentially amplified by the VRP, resulting in the formation of colonies of RNAs that contain short "replicas" of the target molecule within their sequences (see the bottom diagrams in FIGS. 3A and 3B). The positive colonies are identified and distinguished from the colonies comprised of contaminating replicating RNAs by hybridizing the substrate membrane or a replica membrane with a labeled oligonucleotide probe which is complementary to the target-related segment of the replicatable probe, as described in Example 1(b). It is also possible to detect different targets in one assay by using a mixture of the corresponding binary probes and hybridizing the membranes with the labeled oligonucleotides directed against each of those targets.

EXAMPLE 5

Application of the Method of Amplification of Nucleic Acids in Immobilized Media for in vitro Cloning In this example, a procedure based on DNA amplification in PCR is described. Of course, 3SR and VRP reactions can also be employed. In the case of VRP amplification, the procedure uses thie extension of binary probes (as described in Example 4 and depicted in FIG. 3B) targeted to the ends of a DNA or RNA to be cloned (these can also be the universal terminal extensions, see below) to produce a recombinant replicating RNA molecule that carries the foreign sequence included between the target sites.

In the conventional PCR format, a desired sequence from a mixture of nucleic acids can be specifically amplified by using two unique primers that embrace that sequence. Employing the technique of carrying PCR in immobilized media allows any sequence to be cloned with two universal primers, without the need for synthesizing a new pair of unique primers for every new fragment to be amplified. The method comprises preparing a mixture of nucleic acid fragments whose size is within the range amplifiable by PCR (i.e., up to 10 kb), providing the fragments with universal terminal extensions, and amplifying the fragments employing the primers that are complementary to the extensions. In this format, every fragment that is present in the mixture is capable of amplification, and every fragment will give rise to a colony when PCR amplification is carried out in a thin layer of an immobilized medium. The next step is identifying the colony or colonies containing the progeny of a particular fragment and obtaining DNA from that colony for further amplification and use.

The original mixture can be, for example, the fragments obtained by digesting a genomic DNA with a restriction endonuclease [Kessler, C. and Holtke, H. J. (1986). Specificity of Restriction Endonucleases and Methylases—A Review. Gene 47, 1–153], or a mixture of cDNA copies of cytoplasmic mRNAs [Williams, J. G. (1981). The Preparation and Screening of a cDNA Clone Bank. In Genetic Engineering 1 (ed. by R. Williamson), pp. 1–59, Academic Press, London]. The fragment ends are provided with universal terminal extensions by ligating oligonucleotides or by addition of homopolynucleotide tails. It is preferred that the 5' and 3' ends receive different and non-complementary extensions. This can be achieved, for example, by extending the 3' ends through ligation of the double-stranded DNA fragments with 5'-phosphorylated oligodeoxyribonucleotide adaptors that are compatible with the fragment ends, or through addition of a homopolynucleotide tail [Sambrook et al. (1989), supra], and extending the 5' ends through ligation of the DNA strands with oligoribonucleotides [Higgins, N. P., Gebale, A. P. and Cozzarelli, N. R. (1979). Addition of oligonucleotides to the 5'-Terminus of DNA by T4 RNA Ligase. Nucleic Acids Res. 6, 1013–1024].

After the DNA fragments have been amplified in a thin layer of an immobilized medium as described in Example 3 to obtain single colonies, the colonies are screened for a particular fragment by an appropriate method. This can be the hybridization with specific probes targeted against an internal region of the fragment, carried out as described above, if a partial sequence of the corresponding gene or of its homologous gene from another source is known. Alternatively, the gene can be located by detecting the products of its expression. A technique described by Benton and Davis can be employed to precisely localize the identified colonies in the PCR gel [Benton, W. D. and Davis, R. W. (1977). Screening λgt Recombinant Clones by Hybridization to Single Plaques in situ. Science 196, 180–182].

EXAMPLE 6

Expression in an Immobilized Medium of the Nucleic Acids Cloned in vitro

If PCR is used for cloning DNA fragments, an RNA polymerase promoter sequence, such as a SP6 or T7 promoter, is included in one of the terminal extensions as described in Example 5. Grown colonies are contacted with an immobilized expression layer containing all the components of a coupled transcription/translation system [Tymms, M. J. and McInnes, B. (1988). Efficient in vitro Expression of Interferon Analogs Using SP6 Polymerase and Rabbit Reticulocyte Lysate. Gene Anal. Tech. 5, 9–15; Baranov, V. I., Morozov, I. Yu., Ortlepp, S. A. and Spirin, A. S. (1989). Gene Expression in a Cell-free System on the Preparative Scale, Gene 84, 463–466]. This can be done either by putting the expression layer atop the PCR layer, or by transferring DNA colonies from the PCR layer to the expression layer by means of a blotting membrane. After the expression reaction is completed, the expression products are screened in situ for their ability to carry out enzymatic reactions or for their ability to bind specific ligands or antibodies.

For example, clones carrying a phosphatase gene can be detected by transferring the expression products onto a blotting membrane which is soaked with a 5-bromo-4-chloro-3-indolyl phosphate:nitroblue tetrazolium solution. In the locations where a phosphatase is present, a purple color is developed [Leary, J. J., Brigati, D. J. and Ward, D. C. (1983). Rapid and Sensitive Colorimetric Method for Visualizing Biotin-labeled DNA Probes Hybridized to DNA or RNA immobilized on Nitrocellulose: Bio-blots. Proc. Natl. Acad. Sci. U.S.A. 80, 4045–4049]. Genes encoding photoproteins such as apo-obelin (from hydroid Obelia geniculata) can be detected by luminescence [Campbell, A. K., Patel, A. K., Razavi, Z. S. and McCapra, F. (1988). Formation of the $Ca^{2+}$-activated Photoprotein Obelin from Apo-obelin and mRNA Inside Human Neurophils. Biochem. J. 252, 143–149]. In this case, the protein prostatic group coelenterazine is introduced into the expression gel that is cast on a transparent support and, after being incubated during an hour to synthesize proteins, the gel is mounted on a photographic film with the support side facing down and is overlaid with a membrane impregnated with $Ca^{2+}$. Diffusion into the gel and binding of $Ca^{2+}$ with obelin (apo-obelin: coelenterazine complex) causes luminescence and hence illumination of the photosensitive film at the locations where apo-obelin has been synthesized.

Alternatively, expression products can be screened with a variety of immunochemical methods. Of these, the most preferable are the very sensitive methods employing chemiluminescent reactions performed by alkaline phosphatase and horse radish peroxidase. Corresponding assay kits are commercially available, e.g. from the United States Biochemical Corporation and Amersham International plc, respectively.

We claim:

1. A method of detecting a nucleic acid sequence in a sample that may contain said sequence comprising the steps of:
   (a) providing a cell-free, enzymatic, exponential amplification system;
   (b) forming a liquid mixture of the sample and said amplification system;
   (c) entrapping said liquid within solid surfaces comprising a thin layer;
   (d) incubating said trapped mixture under conditions promoting synthesis of an exponentially amplified nucleic acid product from said nucleic acid sequence; and
   (e) screening to detect said amplified product,
   wherein the average distance between the nearest solid surfaces is smaller than the distance which the synthesized nucleic acid product can migrate by diffusion during the reaction, and
   wherein copies of said nucleic acid sequence, if present in said sample, are sufficiently widely distributed in said liquid mixture to produce separate, detectable colonies of the synthesized nucleic acid product.

2. The method of claim 1, wherein said average distance is from 5 nm to 100 $\mu$m.

3. The method of claim 2, wherein said solid surfaces comprise a solid matrix selected from the group consisting of agarose, polyacrylamide, nylon, gelatin, alginate, carrageenan, cellulose, silica gel, titanium sponge, dextran, and polyethylene glycol.

4. The method of claim 3, wherein said matrix is chemically modified with hydrophobic and positively charged groups.

5. The method of claim 3, wherein said matrix is chemically modified with weak cationic groups selected from the group consisting of secondary and tertiary amino groups.

6. The method of claim 3, wherein said matrix has a thickness of from 1 $\mu$m to 10 mm.

7. The method of claim 1, wherein said step of screening comprises visualizing detectable colonies with an intercalating dye.

8. The method claim 1, wherein said step of screening comprises the steps of:
   (a) expressing the synthesized nucleic acid product; and
   (b) identifying an expression product.

9. The method of claim 8, wherein said expressing is by a cell-free expression system.

10. The method of claim 8, wherein the step of identifying an expression product is performed in the immobilized medium by carrying out a reaction selected from the group consisting of a specific enzymatic reaction, binding of a specific ligand, and a specific immunochemical reaction.

11. The method of claim 1, wherein said amplification system includes at least one nucleoside triphosphate bearing a label and said step of screening comprises detecting said label.

12. The method of claim 1, wherein said step of screening comprises contacting said synthesized nucleic acid product with a labeled oligonucleotide probe and detecting said label.

13. The method of claim 1, wherein said amplification system is a Viral RNA Polymerase system.

14. The method of claim 1, wherein said amplification system is a 3SR Amplification system.

15. The method of claim 1, wherein said amplification system is a Polymerase Chain Reaction system and wherein said step (c) comprises cycling the medium through at least 2 temperatures.

16. The method of claim 1, wherein said amplification system comprises nucleotide substrates selected from the group consisting of ribonucleotides, deoxyribonucleotides, and both ribonucleotides and deoxyribonucleotides.

17. A method of detecting a nucleic acid sequence in a sample that may contain said sequence comprising the steps of:
   (a) providing an immobilized medium, said medium including
      (i) an aqueous liquid phase that includes a cell-free, enzymatic, exponential nucleic acid amplification system; and
      (ii) a solid, water-insoluble matrix having an average pore size ranging from 100 $\mu$m to 5 nm, completely entrapping said liquid phase,
   (b) distributing in said aqueous liquid phase nucleic acid molecules, at least one of which may comprise a template for said amplification system;
   (c) incubating said immobilized medium containing said distributed molecules under conditions promoting synthesis of an exponentially amplified nucleic acid product by said amplification system from said at least one template; and
   (d) screening said colonies,
   wherein said matrix is stable under said conditions, and wherein said step of distributing separates individual templates, resulting in nucleic acid amplification to form at least one separate, detectable colony of said nucleic acid product in said medium.

18. The method of claim 17, wherein the immobilized medium is shaped into at least one thin layer.

19. The method of claim 17, wherein said amplification system is a Viral Polymerase system.

20. The method of claim 17, wherein said amplification is a Polymerase Chain Reaction system and wherein step (c) includes cycling the medium through at least two temperatures.

21. The method of claim 17, wherein step (a) precedes step (b).

22. The method of claim 17, wherein said screening is in a screening medium, said screening occurring after transfer of said at least one colony from said immobilized medium to said expression medium.

23. The method of claim 17, wherein said step of screening comprises hybridizing with a labeled oligonucleotide probe and detecting said label.

24. A method of detecting a nucleic acid sequence in a sample that may contain said sequence comprising the steps of:
 (a) providing a first solid, water insoluble matrix layer having an average pore size ranging from 100 µm to 5 nm and containing a first portion of the components of a cell-free enzymatic, exponential nucleic acid amplification system;
 (b) providing a second solid, water-insoluble matrix layer having an average pore size ranging from 100 µm to 5 nm and containing a second portion of the components of said amplification system, said first and second portions together comprising said amplification system;
 (c) distributing on at least one of said matrix layers nucleic acid molecules, at least one of which may comprise a template for said amplification system;
 (d) contacting said first and second matrix layers, sandwiching said nucleic acid molecules between said layers;
 (e) incubating said first and second matrix layers while maintaining contact therebetween under conditions promoting synthesis of an exponentially amplified nucleic acid product by said amplification system from said at last one template; and
 (f) screening said nucleic acid product,
 wherein said first and second matrix layers are stable under said conditions; wherein said conditions cause at least said first portion or said second portion of said amplification to diffuse from one of said matrix layers into the other, together with said nucleic acid molecules; and wherein said distribution of nucleic acid molecules separates individual templates, resulting in nucleic acid amplification to form at least one separate, detectable colony of said nucleic acid product in at least one of said first and second matrix layers.

25. The method of claim 24, wherein said second portion of the reaction components of said amplification system includes all enzymes of said amplification system and wherein, during said step (e) of incubating, said second matrix layer is contacted with at least one blotting membrane, and amplified product transfers to said at least one blotting membrane.

* * * * *